US00PP07925P

United States Patent [19]

van Andel

[11] Patent Number: Plant 7,925

[45] Date of Patent: Jul. 28, 1992

[54] ALSTROEMERIA NAMED STAVERPI

[75] Inventor: Jacob van Andel, Aalsmeer, Netherlands

[73] Assignee: Van Staaveren B.V., Aalsmeer, Netherlands

[21] Appl. No.: 560,098

[22] Filed: Jul. 30, 1990

[51] Int. Cl.[5] ..... A01H 5/00

[52] U.S. Cl. ..... Plt./87.1

[58] Field of Search ..... Plt./68, 87.1

*Primary Examiner*—Howard J. Locker

[57] ABSTRACT

A new Alstroemeria cultivar characterized by the Venetian Pink coloration of the outer tier of the flower petals and the general Buttercup Yellow coloration of the inner petals which are particularly characterized by short brown pencil stripes which appear in longitudinal rows extending from end to end of these petals, and by its vigorous upright growth habit with more or less continuous production of flowers on each branch during each of its recurrent blooming seasons.

1 Drawing Sheet

BACKGROUND OF THE NEW PLANT

This new Alstroemeria cultivar originated as a hybrid seedling produced by me by crossing unpatented varieties selected from my breeding stock maintained at our nursery at Aalsmeer, Holland, with the object of producing new flower colors and improved winter production under Dutch glass house conditions, this particular seedling having been selected for propagation and test because of its profuse production of very large flowers on a tall vigorous upright bush having a rapid growth rate. The selected seedling was propagated at Aalsmeer by its roots with such pleasing results that propagation by that method was carried on at Aalsmeer through several successive generations which demonstrated clearly that the distinctive characteristics of the original seedling hold true from generation to generation and appear to be firmly fixed. Propagation of this new variety is now being carried on at Aalsmeer, Holland by dividing rhizomes.

DESCRIPTION OF THE DRAWING

This new Alstroemeria cultivar is illustrated by the accompanying photographic drawing which is a black and white rendition of a group of blooms which has been hand painted in part to show the coloring and the form of the individual flowers.

DESCRIPTION OF THE NEW PLANT

The following is a detailed description of my new Alstroemeria cultivar as observed in greenhouse at Aalsmeer, with color designations according to the R.H.S. Colour Chart of The Royal Horticultural Society of London, England.

THE PLANT

Origin: A hybrid seedling.

Hybrid parentage:

*Seed parent.*—Edison (unpatented).

*Pollen parent.*—Plant No. 4345-1 from breeding stock.

Both parents are identified in our breeding records maintained in nursery office at Aalsmeer.

Classification:

*Botanic.*—Alstroemeria hybrid.

*Commercial.*—Alstroemeria.

Form: A tall, upright, strong and vigorous bush.

Height: About 180 cm.

Growth rate: Fast.

Main stem length: About 180 cm.

Branching character: Each flower stalk branches at the top into about six flower-bearing stems.

Foliage:

*Quantity.*—Normal.

*Number of leaves.*—Varying with the season.

*Size of leaf.*—Medium.

*Leaf shape.*—Elliptic.

*Texture.*—Smooth.

*Color.*—Upper side — Middle green. Under side — Grey green.

Rhizomes:

*Color.*—White.

THE BUD

Size: Medium.

*Diameter.*—2 cm.

*Length.*—4 cm.

Form: Pear-shaped.

Peduncle of flower:

*Length.*—About 5 to 12 cm. depending upon season.

*Color.*—Dark green.

THE INFLORESCENCE

Blooming habit: Recurrent and profusely during Spring and Fall blooming seasons.

Flower size: Very large.

*Diameter.*—About 70 mm.

*Depth.*—About 60 mm.

Borne: Singly.

Shape:

*When bloom first opens.*—Cup shaped.

*When bloom matures.*—Generally funnel-like.

Petalage:

*Number of petals.*—6.

*Arrangement.*—Two concentric circles of three.

*Form.*—Obovate and slightly serrated margins.

*Texture.*—Soft.

*Appearance.*—Satiny.

*Color.*—Outer petals — body, 49-C; base, 49-B, and reverse side, Neyron Rose 55-C. Outer petals have few short brown pencil stripes, located in the central area thereof. Inside petals — body generally, 15-B with Neyron Rose, 55-C at top end. Inside petals have numerous short brown pencil stripes which appear in longitudinal rows from end to end of the petals.

Flower stem:

*Length.*—1.5 to 4 cm.

*Color.*—Dark green.

*Character.*—Strong and upright.

Effect of wet or hot weather: None.

Persistence: The flowers hang on and dry.

Fragrance: None.

Lasting quality:

*On plant.*—20 days.

*As cut flower.*—14 days.

THE REPRODUCTIVE ORGANS

Stamens:

*Number.*—Six.

*Arrangement.*—One opposite each petal.

*Anthers.*—Size: 8 to 10 mm. Color: Green/yellow.

*Filaments.*—Length: About 50 mm. Color: Salmon pink.

*Pollen.*—Color: Yellow.

Pistils:

*Number.*—One.

*Style.*—Length: About 45 mm. Color: Salmon.

*Stigma.*—Color: Salmon.

This new Alstroemeria cultivar most nearly resembles the variety Staronic, U.S. Plant Pat. No. 6,474, but differs with respect to color, flower shape and growth habit.

I claim:

1. The new and distinct Alstroemeria cultivar, substantially as herein shown and described, characterized by the Venetian Pink coloring of its flowers each of which is supported by a strong, sturdy and long peduncle.

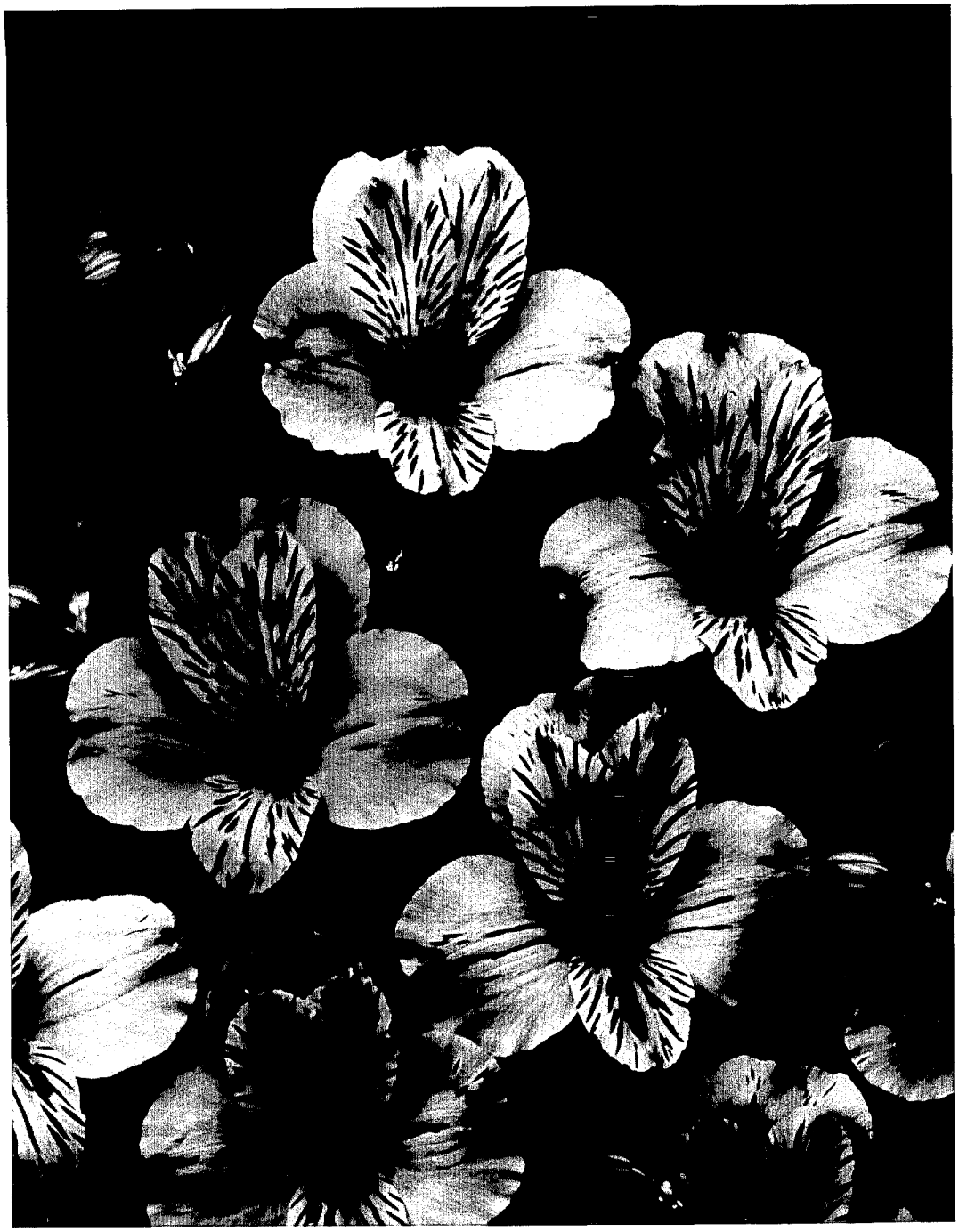

* * * * *